US007576343B2

(12) United States Patent
Tomie

(10) Patent No.: US 7,576,343 B2
(45) Date of Patent: Aug. 18, 2009

(54) METHOD AND APPARATUS FOR GENERATING LASER PRODUCED PLASMA

(75) Inventor: Toshihisa Tomie, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 62 days.

(21) Appl. No.: 10/550,413

(22) PCT Filed: Mar. 24, 2004

(86) PCT No.: PCT/JP2004/004031

§ 371 (c)(1), (2), (4) Date: Jul. 18, 2006

(87) PCT Pub. No.: WO2004/100621

PCT Pub. Date: Nov. 18, 2004

(65) Prior Publication Data

US 2007/0158577 A1 Jul. 12, 2007

(30) Foreign Application Priority Data

Mar. 24, 2003 (JP) ............................. 2003-080378

(51) Int. Cl.
*A61N 5/06* (2006.01)
*G01J 3/10* (2006.01)
*H05G 2/00* (2006.01)

(52) U.S. Cl. ............................... 250/504 R; 250/505.1; 250/492.2; 250/492.1; 250/461.1; 378/119; 378/143; 378/34; 772/5

(58) Field of Classification Search ............. 250/504 R, 250/505.1, 492.2, 492.1, 461.1; 378/119, 378/143, 34; 772/5
See application file for complete search history.

(56) References Cited

U.S. PATENT DOCUMENTS 6,002,744 A * 12/1999 Hertz et al. ................. 378/119

(Continued)

FOREIGN PATENT DOCUMENTS

JP 11-250842 9/1999

(Continued)

OTHER PUBLICATIONS

Sugar, Jack: "Potential-Barrier Effects in Photoabsorption. II. Interpretation of Photoabsorption Resonances in Lanthanide Metals at the 4*d*-Electron Threshold", Physical Review B, vol. 5, No. 5, pp. 1785-1792, 1972.

(Continued)

*Primary Examiner*—Jack I Berman
*Assistant Examiner*—Meenakshi S Sahu
(74) *Attorney, Agent, or Firm*—Oblon, Spivak, McClelland, Maier & Neustadt, P.C.

(57) ABSTRACT

The present invention provides a method of delivering solid material at a position far enough from any surrounding solid with high enough target density without scattering debris to the environment. In the present invention, radiation is generated from plasma produced by laser irradiation on a material. This material is a cluster of particles that is composed of many fine particles bound together with a binder that vaporizes at temperature lower than melting point of fine particles. Density of particles in a particle-cluster 8 is increased by vaporizing a solvent 7 by heating a droplet 5 with the irradiation of laser 6. Solvent of a droplet occupies large fraction of the droplet in order to stabilize droplet generation. This solvent is vaporized prior to delivery to a vacuum chamber 9 for plasma generation. This vaporization helps to avoid degradation of vacuum of the chamber 9. The diameter of a particle-cluster thus condensed is several tens μm.

34 Claims, 6 Drawing Sheets

Production of droplets of suspension including ultrafine particles

U.S. PATENT DOCUMENTS

| | | | | |
|---|---|---|---|---|
| 6,507,641 | B1 | 1/2003 | Kondo et al. | |
| 6,814,239 | B2 | 11/2004 | Suzuki et al. | |
| 6,831,963 | B2 * | 12/2004 | Richardson | 378/119 |

FOREIGN PATENT DOCUMENTS

| | | |
|---|---|---|
| JP | 2000-91095 | 3/2000 |
| JP | 2000-215998 | 8/2000 |
| JP | 2001-108799 | 4/2001 |
| JP | 2002-8891 | 1/2002 |
| JP | 2002-239377 | 8/2002 |
| WO | 02/46839 | 6/2002 |

OTHER PUBLICATIONS

O'Sullivan, G. et al: "4*d*-4*f* emission resonances in laser-produced plasmas", Journal of Optical Society of America, vol. 71, No. 3, pp. 227-230, 1981.

Bender, H.A. et al.: "Velocity characterization of particulate debris from laser-produced plasmas used for extreme-ultraviolet lithography", Applied Optics, vol. 34, No. 28, pp. 6513-6521, 1995.

"Theoretical consideration on power limit of EUV source", National Institute of Advanced Industrial Science and Technology, AIST01-A00007, Ver. 1.1. pp. 1-30, 2002. (with partial English translation).

Schwenn, U. et al.: "A Continuous droplet source for plasma production with pulse laser", Journal of Physics E: Scientific Instruments, vol. 7, p. 715-718, 1974.

Rymell, L. et al.: "Droplet target for low-debris laser-plasma soft X-ray generation", Optics Communications, vol. 103, No. 1-2, pp. 105-110, 1993.

Eickmans, Johannes H. et al.: "Plasma spectroscopy H, Li, and Na in plumes resulting from laser-induced droplet explosion", Applied Optics, vol. 26, No. 17, pp. 3721-3725, 1987.

Tompkins, R.J. et al.: "5-20 keV laser-induced x-ray generation at 1 kHz from a liquid-jet target", Review of Scientific Instruments, vol. 69, No. 9, pp. 3113-3117, 1998.

* cited by examiner

Temporal progress of density profile when sphere target of 20 μm diameter is irradiated with laser Temporal progress of density profile when sphere target of 20 μm diameter is irradiated with laser Production of droplets of suspension including ultrafine particles Formation of particle-cluster Dispersed particles of cluster strongly irradiated with pulsed laser Control of trajectory of particle-cluster

METHOD AND APPARATUS FOR GENERATING LASER PRODUCED PLASMA

FIELD OF THE INVENTION

The present invention relates to a method and an apparatus for generating a laser-produced plasma for generating radiation by irradiating a pulsed laser on materials.

BACKGROUND ART

An object of the present invention is to provide a method for delivering chemical elements, which exists in a form of a solid at room temperature, as a target of a plasma for many hours consecutively, and to provide a plasma radiation source using this target.

A high-temperature and high-density laser-produced plasma (LPP) which is produced by irradiating a pulsed laser on a material is a highly brilliant radiation source covering from extreme ultraviolet (EUV) region to x-ray region. Spectral structure of the emission from a plasma depends largely on laser irradiation conditions and atomic elements in a plasma. Hence, the best target material for a plasma and laser irradiation conditions should be optimized in each application.

For example, EUV lithography (EUVL) which uses an EUV light of wavelength around 13.5 nm as an illumination light is considered the most promising lithography technology for fabricating semiconductor devices with a feature size of 45 nm and below. A plasma is the unique source for EUVL. Multilayer mirror employed in EUVL is a Mo/Si multilayer. The peak reflection wavelength of the mirror is around 13.5 nm with the reflection bandwidth of 2%. Therefore, a source for EUVL should have an appropriate spectrum matching this property of the Mo/Si mirror.

By the works started by Sugar in 1970's [non-patent reference 1] followed by O'Sullivan in 1980's [non-patent reference 2], it was made clear that 4d-4f band emission is the best to be used when a plasma is employed as a source of several % bandwidth. It was made clear that the peak wavelength of 4d-4f transitions was determined by the atomic number. The element which has the radiation peak at 13 nm was found to be tin, Sn, having the atomic number of 50. Therefore, it is obvious that the best element for an EUVL source requiring 13 nm radiation is Sn.

However, Xe continued to be the only one element as a material of the plasma in developments performed in US and Europe. Atomic number of Xe is 54 and the wavelength of 4d-4f band is around 11 nm, and the emission at around 13 nm is not strong. The reason why Xe is employed in spite of weak emission at 13 nm is the following. In EUV lithography, lifetime of an optic collecting radiation from a LPP is required to be longer than one year, i.e., more than 1E12 shots. Hence, a plasma for EUVL is required to be ultra clean. It is well known that tremendous amount of small particles of μm size, called debris, are generated when a plasma is generated on a solid plate. Debris contaminate and damage surrounding optics heavily. In mid 1990's, some methods of reducing debris, such as use of a tape target or a gas flow were tried. However, it was judged that a LPP on a solid target cannot be the source for EUVL [non-patent reference 3]. On the other hand, it was expected that damage to optics would be negligible with a Xe plasma because Xe exists as a gas at room temperature and Xe does not stick to optics. Actually, damage due to sticking is not observed for a Xe plasma.

As such, technologies using a Xe plasma has been developed. However, lately use of a Sn plasma is becoming inevitable, owing to jumping-up increase of source power requirement from a few watts several years ago to more than 100 W due to many reasons. When a Xe plasma of having a low conversion efficiency is employed, a considerably large power is required for a pumping laser. Here, CE is defined as a ratio of useable energy at 13 nm to the deposited laser energy. Then, cost of pumping laser becomes huge. Moreover, cooling of vacuum space in which a plasma is generated will become technologically very difficult. Even a tin plasma is employed by expecting a higher CE, it cannot be a source for EUVL if the debris issue is not solved. Because it was judged near ten years ago that debris issue could not be solved, a totally new idea must be devised.

(Required Minimum Mass)

First, we need to know the minimum mass to deliver. The present inventor has made a detailed theoretical consideration on a plasma source for EUVL [non-patent reference 4]. According to this consideration, the electron temperature should be 30-50 eV, the diameter should be around 500 μm, and the electron density should be around $1E20/cm^3$. In the case of Sn the best element for a 13 nm radiation source, the ionization degree is about 8, then, the mass required is calculated as, $$1\times10^{20}\times(1/8)\times100\times(1/2)/20^3\times1/(6\times10^{23})=1.2\times10^{-7}\text{ g}$$

and it is 0.1 μg. It is about the same mass with that of a solid Sn sphere of 30 μm in diameter.

From this calculation, in order to generate a plasma with the uniform electron density of $1E20/cm^3$ having several hundreds μm diameter, we need to deliver a target material of total mass equal to that of a solid sphere of several tens μm diameter.

(Mixing in a Xe Gas)

Mixing $SnO_2$ nano-particles in a Xe gas flow was proposed by Matsui et al. [patent reference 1] expecting enhancement of 13 nm radiation. However, there are two serious problems in this proposal. The first is that particles conveyed in a gas flow cannot be confined in a small region and scatter to a wide region. When a plasma is generated, scattering of particles in a gas flow is amplified by a pressure of the plasma reaching 10,000 atmospheric pressure. Because of this, environment is heavily contaminated and surrounding material is damaged. The second is that density of particles is very low because of large scattering and that it is nearly impossible to generate a high-density plasma required for a high brilliant plasma. In short, with a method of mixing of Sn particles in a Xe gas flow, debris-freeness is very difficult to realize due to scattering of particles and enhancement of 13 nm radiation is not obtained due to low density of deliverable particle density.

(Droplet of a Solution)

Use of a droplet was also considered. When a gas target is used, gas expands after being ejected through a nozzle and the density decreases very quickly. Even in the case of a Xe LPP, performance is improved by using adiabatic cooling of the ejected gas or by using a liquefied Xe. However, when using a liquid, a liquid jet breaks up due to the growth of fluid instability, and it is not easy to extend the length of a continuous jet longer than 1 cm. Because break-up of a jet takes place randomly, droplet generation is out of control. There is a method of giving a forced vibration to the nozzle to actively control droplet generation. Once a droplet is formed, it flies long distance without breaking-up, and stable delivery of a target material becomes possible.

Use of a droplet target for a LPP generation was tried many years ago in 1973. As a means of delivering a target for laser-fusion, there was a proposal of using a solid pellet. As an alternative, Schwenn and Sigel [non-patent reference 5] proposed use of a droplet target and reported an experiment. From these previous studies, it will be obvious to ordinary experts in laser-plasma research, to use a droplet as a target of a LPP for the purpose of reducing debris. Actually in 1990's, Herz et al. [for example, non-patent reference 3] have performed x-ray generation experiments by using droplets.

It is a common knowledge among specialists in this field that x-ray wavelength depends largely on chemical elements of a plasma. A carbon plasma is employed for generation of a 3.37 nm radiation and an oxygen plasma for a 2.2 nm radiation. As a purpose of evaluating the electron density and electron temperature, Eickmans et al. [7] generated a plasma on a droplet of a water solution including LiCl or NaCl. Therefore, it is obvious for ordinary skilled researchers to use a solution including chemical elements such as Na or Mg when they need emission from a plasma having these elements. Actually, a droplet of an ethylene glycol solution in which copper nitrate is dissolved was irradiated to generate 5 to 20 keV photons emitted from a copper plasma at 1 kHz repetition rate [8]. As such, it is obvious to employ a solution such as tin nitrate or tin sulfate as a solution of droplet target because we know Sn is the best for generation of 13 nm radiation. However, there exist two problems in using a simple solution including Sn. The first problem is that a plasma of a uniform density distribution cannot be generated from a droplet. The second problem is that the source chamber is difficult to achieve high vacuum. With a single particle, a plasma of a large diameter with uniform distribution can not be generated.

FIG. 1 shows temporal change of density distribution of a plasma generated on a solid plate when irradiated by a 1 μm wavelength laser calculated using a 1-dimensopnal hydrodynamic simulation code. Material heated by absorbing a laser energy blows out into vacuum and the solid target is ablated (scraped) with a speed of the order of several tens nm/ns. However, as seen in FIG. 2, the size of the strong emission region having the density of around 3E-3 g/cm$^3$ does not change so much. This tells us that when a diameter of a solid target is larger than several tens μm, as seen in FIG. 1, while a target becomes thinner with time, there always exists solid-state density region, a plasma of uniform density distribution is never created. The density region near critical density where emission is strong does not expand, and the emission region around 3E-3 g/cm$^3$ stays near the initial radius of the target.

Then, in order to produce a high brilliant source with a diameter of 500 μm, the diameter of a droplet needs to be 500 μm. Because only the surface of a solid target with thickness about 1 μm is converted to a plasma, 100 times larger mass than necessary is delivered into a source chamber. This situation is not good because it increases contamination material. This material contaminates surrounding optics and causes absorption of EUV emission.

In order to keep the transmission of EUV light higher than 90%, pressure of oxygen in the source chamber needs to be lower than 0.1 Pa. When the diameter of a droplet is 500 μm and when a solvent which occupies most of the volume of a droplet is water, evaporation of solvent water produces oxygen of 5-litter volume at 0.1 Pa. An EUVL source will be required to operate at 10 kHz, and then nitrogen gas of 0.1 Pa pressure will be generated 50,000 litters in 10.000 shots in one second. Pumping this volume is an extremely heavy load to a vacuum pump. The volume of the generated gas is to be reduced to lower than 1/50. If possible, volume to be pumped is desired to be reduced to lower than 1/1,000. This requires the diameter of a droplet to be smaller than 50 μm.

[Patent Reference 1]
U.S. Pat. No. 5,991,360
[Patent Reference 2]
Japanese Patent No. 2897005
[Non-Patent Reference 1]
Sugar; Phys. Rev. B5 (1972) 1785
[Non-Patent Reference 2]
G. O'Sullivan and P. K. Carrol; J. Opt. Soc. Am. 71 (1981) 227
[Non-Patent Reference 3]
H. A. Bender, D. O'Connel and W. T. Silvast; Appli. Opt. 34 (1995) 6513
[Non-Patent Reference 4]
T. Tomie; AIST Report AIST01-A00007, "Technical consideration on a plasma for EUV lithography", January 2001.
[Non-Patent Reference 5]
Schwenn and Sigel; J. Phys. E: Sci. Instrum. 7 (1974) 715
[Non-Patent Reference 6]
Herz et al.; Opt. Commum. 103 (1993) 105
[Non-Patent Reference 7]
Eickmans et al.; Appl. Opt. 26 (1987) 3721
[Non-Patent Reference 8]
R. J. Tomkins et al.; Rev. Sci. Instrum. 69 (1998) 3113

SUMMARY OF THE INVENTION

As described above, in order to maximize CE of EUV radiation emitted from a plasma, the most adequate chemical element needs to be selected for each wavelength of the emission. When the said element exists in a form of a solid at room temperature, the target material should be delivered in a method which does not generate large amount of debris. Although there have been some proposals for solving debris issue, all of them have their own problems and none of them can be a solution.

As a method of debris-free plasma generation, the inventor has proposed a scheme of using a concave structure target [patent reference 1] and has demonstrated debris freeness of the plasma generated in the proposed scheme. However, it was difficult to increase plasma density, which caused a low CE. It was also difficult to make the distance between a plasma and a target large, which difficulty could cause insufficient suppression of debris.

Mixing of $SnO_2$ fine particles in a Xe gas flow was tried by Matsui [Patent reference 1]. However, most of particles delivered by a gas flow were scattered in the chamber and environment was severely contaminated. Moreover, a highly brilliant plasma was not generated because the density of particles delivered in the region for plasma generation is very low. Concerning proposals of using a droplet of a solution, there are problems that a plasma of a uniform density distribution cannot be generated, density of chemical element required is difficult to make high, and high vacuum in the source chamber is very difficult to achieve.

In view of the above drawbacks of the prior arts, an object of the present invention is to provide a method of delivering solid material at a distance far enough from any surrounding solid material with high enough plasma density and without generating particle debris.

In the present invention of laser generation method and apparatus, radiation is generated from a plasma produced by irradiating a laser on a target material. The present invention is characterized in using a particle-cluster as a target which is formed by aggregation of many particles with a molecular force and/or an electrical force among particles, or with a help of a binder which evaporates at temperature lower than a melting temperature of particles.

In the present invention of laser generation method and apparatus, radiation is generated from a plasma produced by irradiating a laser on a, target material. The present invention is characterized in generating fine particles by the irradiation of a short pulse on material under an air flow and in conveying the generated fine particles in a gas flow to a plasma generation region.

DESCRIPTION OF THE PREFERRED EMBODIMENT

The present invention is explained in the following, by showing some examples. Described solvents, materials mixed in a solvent, conditions of droplet generation, method of condensation and others are just a few examples. Variations conceivable by skilled people in each field are adoptable.

Figure 3:
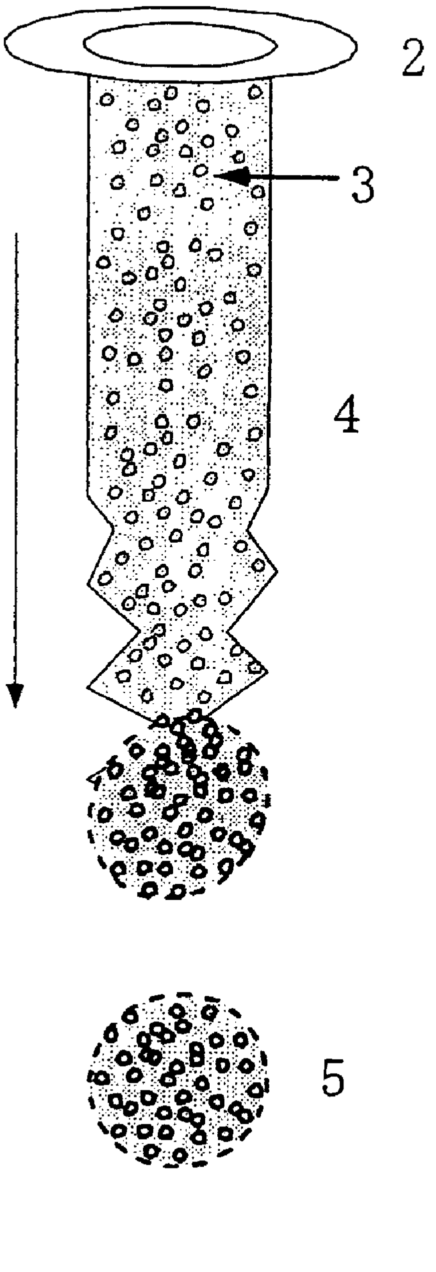
FIG. 3 explains a method of producing droplets of a suspension including fine particles.

FIG. 3 illustrates a method of generating droplets from a suspension including fine particles. As shown in the figure, a suspension liquid containing Sn particles 3 are ejected through a nozzle 2 in a vacuum chamber for droplet generation as a jet of 500 μm to 1 mm in diameter. A forced vibration is given to the nozzle with frequency higher than source repetition frequency. This vibration breaks up the continuous jet 4 to droplets 5. For stable droplet generation, noise vibration caused by vacuum pumps and others to the nozzle should be suppressed and amplitude of a forced vibration needs be larger than turbulent vibration.

In order to achieve concentration of particles constant, potential of Hydrogen of the suspension in a reservoir is adjusted and/or the suspension is stirred.

Figure 4:
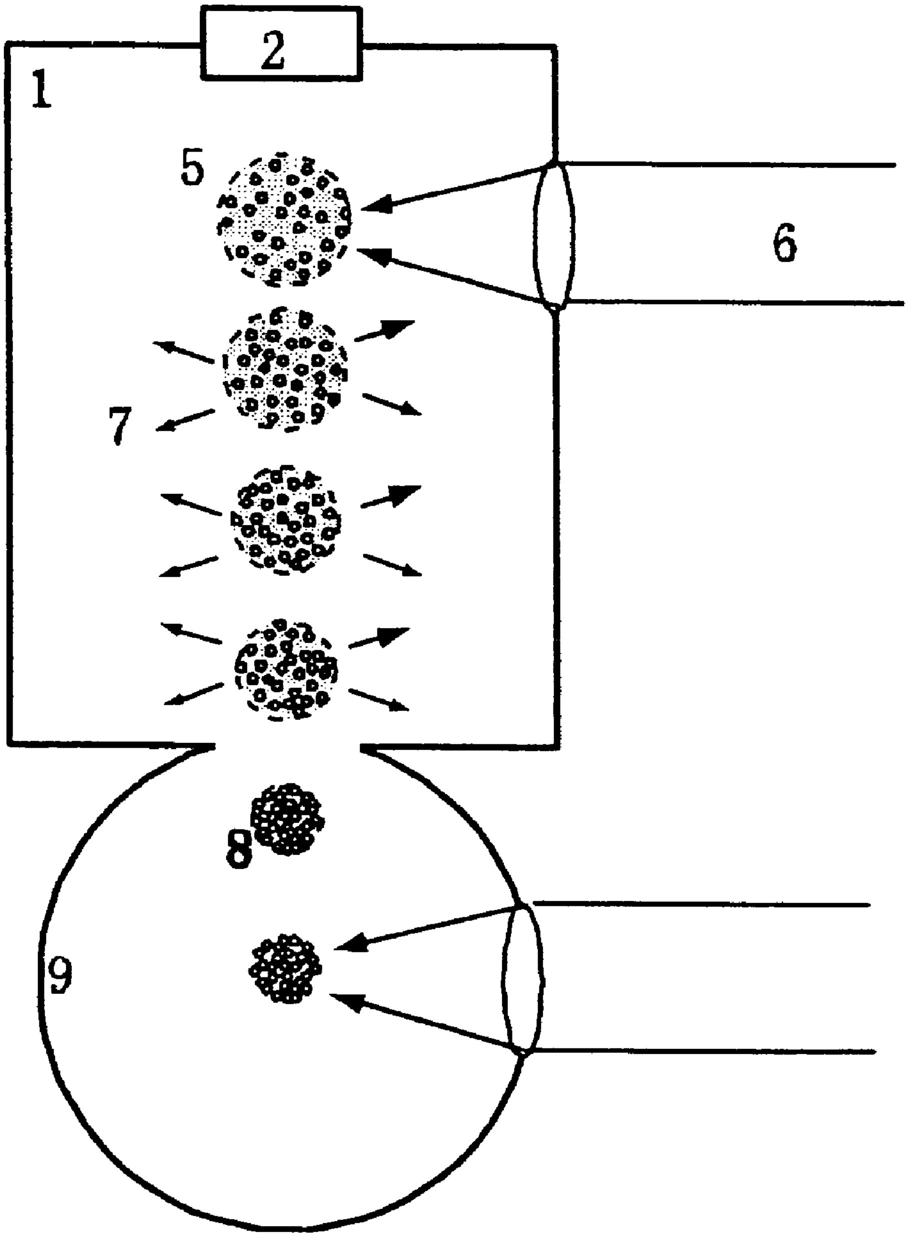
FIG. 4 explains a method of forming a particle-cluster by vaporizing a solvent of a droplet and by condensing the particle density.

FIG. 4 explains a method to form a cluster of particles by vaporizing a solvent of a droplet and condensing particle density. In order to deliver a particle-cluster 8 having a high particle density into a vacuum chamber for plasma generation, laser 6 heats the suspension droplet 5 and solvent 7 of a droplet is vaporized as shown in FIG. 4. Volume of a solvent is large for stabilizing droplet generation. Vaporization of the solvent having a large volume is performed prior to delivery to a vacuum chamber 9 for plasma generation to avoid poor vacuum of the chamber 9. After condensation of a droplet, the diameter of a cluster of particles becomes several tens μm. By vaporizing nearly all solvent as a binder of droplet, the load to vacuum pumps for the chamber 9 is reduced. After total vaporization of the solvent, particles 8 are bound each other to form a particle-cluster by a molecular force or an electrical force among particles.

Vacuum pressure in the chamber 1 for droplet generation will exceed several Pa due to large amount of vaporization of a solvent. On the other hand, vacuum better than 0.1 Pa is required in the chamber 9 for plasma generation. For this purpose, two regions are connected by a small aperture so that differential pumping is effectively performed.

Figure 5:
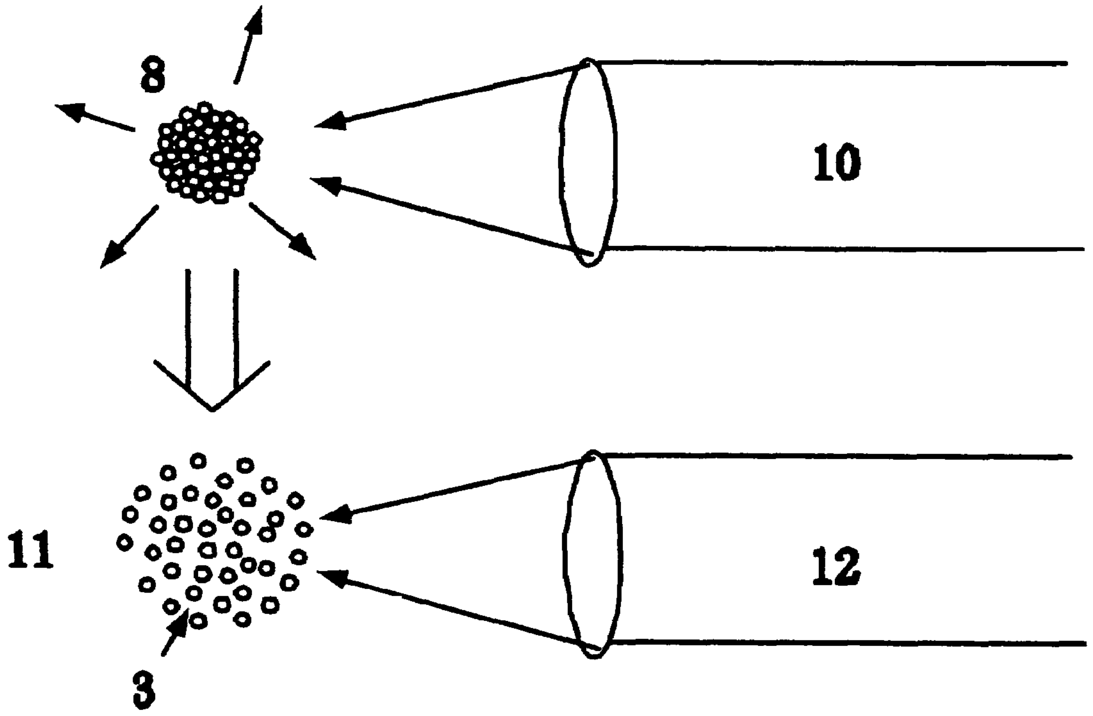
FIG. 5 shows a schematic view of producing a plasma having a large diameter.

FIG. 5 explains how to achieve uniform density distribution of a target material for a plasma generation. For the purpose of generating a uniform plasma, a laser 10 for cracking irradiates a particle-cluster 8 as shown in FIG. 5.

If aggregated particles melt by the irradiation of a cracking laser 10, melted particles merge to form a large single particle that makes formation of a particle-cluster meaningless. In order to give a strong shock to crack a cluster without melting fine particles, an ultra-short pulse laser is better to be employed as a laser 10.

A particle heated by a short pulse expands when temperature rises, and the gravity center shifts by L. When this shift of a gravity center takes place in a short time t, heat expansion generates a large acceleration α. This acceleration exerts force F of $F=mL/t^2$ to a cluster, here m is mass of the particle. Larger force F is created for a shorter temperature rise time t. Therefore, a picoseconds or femtoseconds pulse can generate a large force to crack a cluster. For example, particles larger than 100 nm in diameter gain a force to detach by overcoming a molecular force binding each other when irradiated by a 100 femtosecond laser at the irradiance of 1 $J/cm^2$. Increase of the irradiance proportionally increases the acceleration and gives a stronger shock to a cluster in reaction of the expansion. When the temperature rise is too high, some particles melt and merging of aggregated particles starts. Hence, there is an upper limit in the irradiance. However, we can allow coalescence of particles on the surface of a cluster if whole cluster does not merge to change to a single particle.

At several hundreds ns to several μs after the irradiation of a cracking laser, fine particles 3 are dispersed in a region of several hundreds μm in diameter, and a plasma is generated by irradiating a pulse laser 12. In case of generating a strong 13 nm radiation, best parameters of a plasma is 500 μm in diameter and plasma temperature of 30 to 50 eV. The mass of a particle-duster is adjusted to achieve electron density of $1E20/cm^3$. As a pulse laser, proper parameters for wavelength, pulse energy, and pulse energy are 1 μm, 10 ns, and several tens to several hundreds mJ, respectively.

Figure 6:
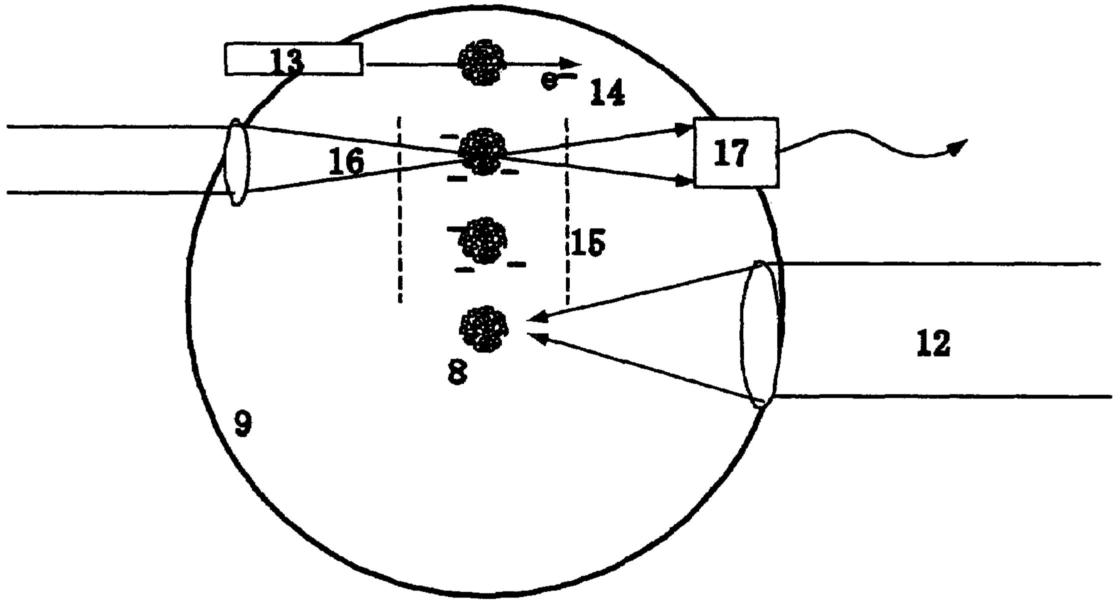
FIG. 6 shows a method of controlling the trajectory of a particle-cluster by electrical method after charging it.

FIG. 6 explains a method of controlling trajectory of a particle-cluster by an electric field. In order to improve accuracy of position for cluster to be delivered, a cluster 8 is charged by charges 14 supplied from an electron gun 13 or an ion gun and the trajectory is controlled by an electrode 15 as shown in FIG. 6.

Timing of droplet generation and velocity of droplets may fluctuate. This can be compensated by observing the passage of a particle-cluster 8 crossing a monitoring CW laser beam 16. The blocking signal from a detector 17 is given to a timing controller to synchronize a laser pulse 12 with the duster 8.

(Aggregation of Fine Particles)

Figure 1:
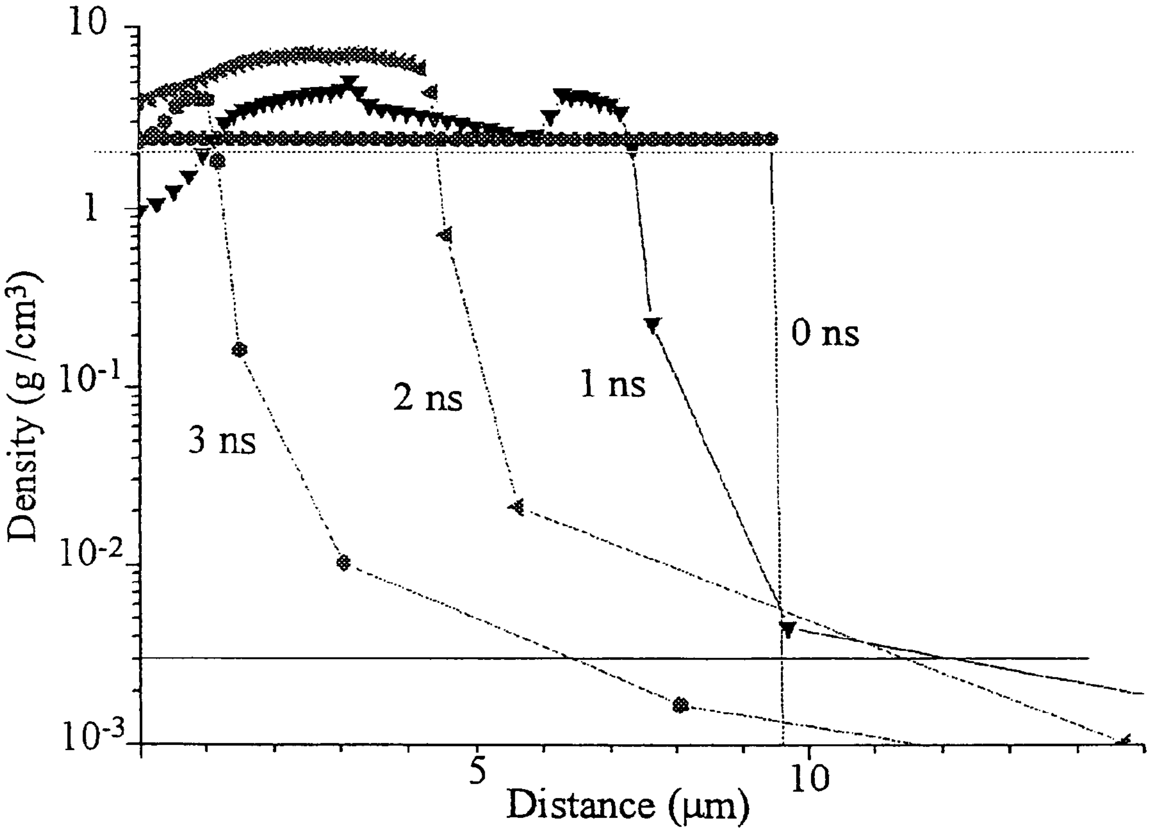
FIG. 1 shows temporal progress of density profile when a solid sphere of 20 μm diameter is irradiated by a laser.
Figure 2:
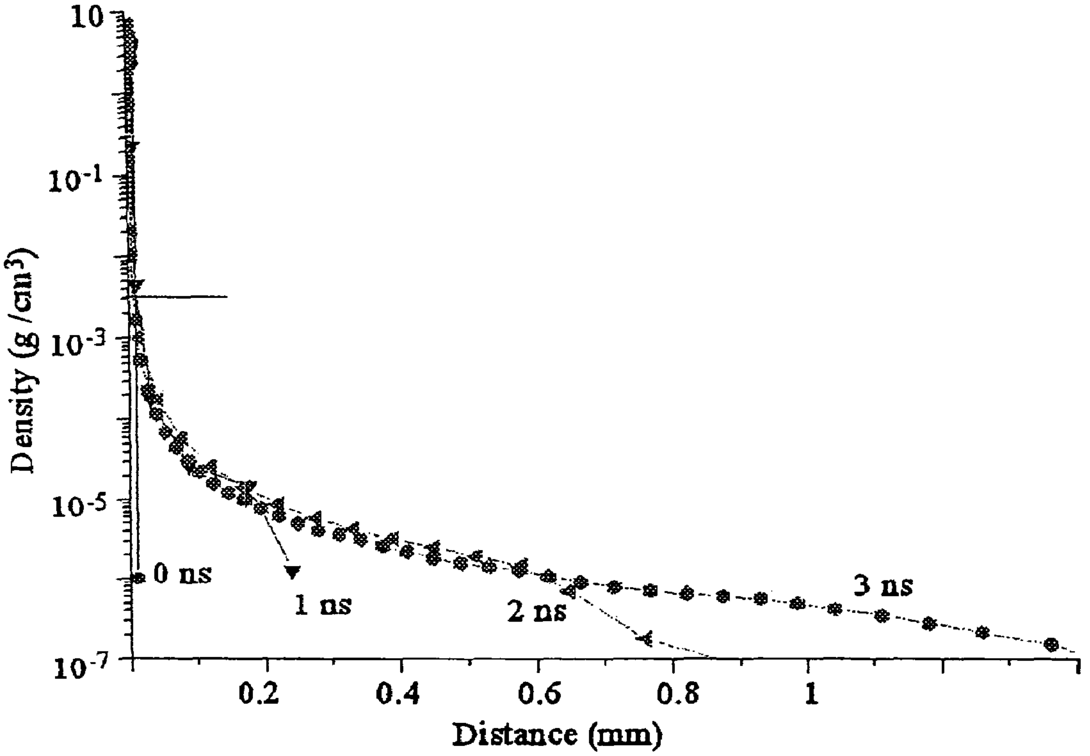
FIG. 2 shows temporal progress of density profile when a solid sphere of 20 μm diameter is irradiated by a laser.

This invention discloses a method of delivering a target material in the form of a duster of many particles. Total mass of the duster is equal to a single sphere of several tens μm in diameter. As seen in FIG. 1, a fine particle smaller than 10 μm in diameter is vaporized without leaving a core of solid density by the irradiation of a several ns pulse. By irradiating a laser after dispersing fine particles uniformly in a region of several hundreds μm in diameter.

A duster can be composed of 27 particles having a 10 μm diameter. However, the number of aggregating particles to form a duster is better to be large in order to have a better density-uniformity of the dispersed particles. When the size of aggregating particles is 1-μm diameter, the number of particles forming a cluster is 20,000 for a cluster to have a weight equal to that of a single sphere of 30 μm diameter.

(Binder)

When the size of constituent particles is 0.1-μm diameter, the number of particles forming a cluster is 3E7 to form a cluster having a weight equal to that of a single sphere of 30 μm diameter. When the size of particles is small, thermal velocity of particles is not small, and particles will disperse to a large region after flying large distance.

Because of this, the present invention provides a method of cohering fine particles with a help of a molecular force, an electrical force or a binder. As a binder, liquid nitrogen, water, organic solvent, and so on can be employed so that the binder does not cause contamination of the source chamber. Particles are mixed in such a solvent to form a suspension. From droplets of this suspension, we can generate particle-clusters of required mass continuously at high repetition rate. In order to reduce fluctuation of total mass of particles in a droplet, particles in a suspension is uniformly dispersed by stirring and other means.

(Vibration)

When a liquid is ejected from a nozzle, the jet is continuous just after the ejection, but it breaks up to small particles after flying a certain distance. The distance of breaking up of a jet depends on a nozzle diameter, ejection speed, and viscosity of a liquid. Break up of a jet to droplets is caused by fluid instability, fluctuation is large, and droplet generation is unstable.

The present invention provides a method of giving a forced vibration to ejected liquid through a nozzle or by other means along the direction of ejection or other arbitrary direction for a stable generation of droplets.

FIG. 3 shows an example of stable generation of droplets by forced vibration (Condensation)

It is not good if the size of a droplet is 500 μm in diameter even when the droplet includes particles of 0.1 μg which is equal to the mass of a sphere of 50 μm diameter of specific gravity of 7. As described before in the DESCRIPTION OF THE PRIOR ART, the diameter of a solvent of a droplet is desired to be smaller than 50 μm for having a good vacuum in the chamber to avoid absorption of EUV light.

On the other hand, for stable generation of droplets, density of particles in a suspension is required to be low enough which requires a droplet to be large. The size of a droplet is about twice of that of an ejected liquid jet. The ratio of separation of droplets and the diameter of droplets is about four, and we cannot make this ratio arbitrarily large.

The present invention provides a method of decreasing a size of a droplet, as shown in FIG. 4, by vaporizing a solvent which increases the density of particles in order to decrease the size of a particle-cluster at the time of plasma generation.

Condensation is performed by vaporization or sublimation of a solvent. The degree of condensation is controlled by controlling temperature of a droplet, and flying distance. Control of temperature can be performed by heating with an infrared heating source or weak laser irradiation or other means. In order to avoid pressure increase of a chamber for plasma generation, condensation is performed in a separate space.

(Guiding of a Particle-Cluster)

Because of many requests, such as condensation of droplets, the distance of plasma generation point from a droplet generation point will be large. Then, droplets may not fly to the pulse laser focusing point. Therefore, as shown in FIG. 6, the present invention provides a method of charging particles by electron shower or other means and a method of electrically controlling the trajectory of droplets.

(Dispersion of Fine Particles)

In order to increase uniformity of plasma density, it is effective to disperse fine particles constituting a cluster prior to the plasma generation. The present invention provides, as shown in FIG. 5, a method of dispersing fine particles forming a cluster to a space of required size.

Because a solvent which serves as a binder is a liquid which exists in a form of liquid or gas at room temperature, heating by an infrared ray or weak laser irradiation vaporizes a solvent of a droplet, and then the suspended particles start to expand. If necessary, fine particles can be heated weakly to become a plasma. By irradiating a pulse laser after fine particles are distributed in a wide region, a plasma of a uniform density distribution can be generated.

The solvent is changed to a plasma in a plasma source chamber. Therefore, liquid nitrogen that has less influence to the environment is appropriate as a solvent of a suspension. Water including oxygen can be employed as a solvent. Depending on other conditions for easy formation solution or easy generation of droplets, organic solvents including carbon or other solvents can be also employed.

(Generation of Fine Particles by Vaporization)

Diameter of fine particles to be mixed in a solvent needs to be small so that core of solid density is not left when irradiated by a laser for a plasma generation. This size depends on laser irradiation conditions and it is about 10 μm or less for a single pulse irradiation. Therefore, if particles are smaller than 10 μm, the density distribution of a generated plasma will be relatively uniform. In order to enhance uniformity, number of aggregating particles is better to be large. There will be cases that the size of particles is desired to be several tens nm to several hundreds nm.

As a method for generating this size ultra-fine particles, we can adopt clustering of vapor atoms composing particles. Particles generated by clustering of vapor atoms can be mixed in a solvent to prepare a suspension.

Another way of preparing a suspension is to send vapor atom directly into a solvent. Vapor atoms form ultra-fine particles in the solvent.

(Generation of Fine Particles by Laser Ablation)

Ultra-fine particles employed in the present invention can be generated by a heat shock induced by pulse laser irradiation. In this case, a pulse laser is irradiated on a tin plate, and melting of the plate and distribution of fine particles can be performed at the same time. In another method, pulse laser irradiation or other pulse heating on a melted tin liquid produces a thermal shock to splash fine particles from the liquid surface.

(Delivery by a Gas Flow)

When the effect of thermal motion is small for large particles and when a delivery distance is not so long, clustering of fine particles for suppressing dispersion of particles is not necessarily required. In this case, in order to reduce number of particles scattered in the environment, delivery of particles is desired to be performed not continuously but pulsively.

Then, the present invention provides a method of generating fine particles of the size larger than 0.1 μm and smaller than 1 μm by laser ablation and a method of delivering these particles by a gas flow.

We have observed generation of fine particles with a distribution peak at 0.2 μm when a pulse laser is irradiated on a solid plate. By performing this laser ablation under a gas flow, generated particles flow with a gas, and particles can be delivered into a plasma generation chamber through a capillary. Many kinds of gases, such as nitrogen, Helium, air and so on can be employed as a conveying gas.

Because wide spread of particles cannot be avoided, the distance of delivery is limited in the case of delivery by a gas flow. However, this scheme of delivering by a gas flow has the advantage that the vacuum pressure might be lowered, while vacuum in the source chamber may be poor in case of delivery by droplets.

In this invention, a target material is delivered in a form of a particle-cluster and this enables delivery of solid material to a position far enough from surrounding solid at high enough density without scattering debris to the environment.

The present invention also enables high repetition rate delivery of a particle-cluster exceeding kHz and high accuracy guiding of clusters to the plasma generation region by generating droplets from a suspension including fine particles followed by forming a particle-cluster by condensing density of particles by vaporizing a solvent.

The present invention also prevents degradation of vacuum of a chamber for plasma generation by vaporizing a solvent of a droplet of a suspension prior to delivery of a particle-cluster into the plasma generation chamber.

The invention claimed is:

1. A method for generating a plasma as a source of radiation by irradiating a pulsed laser on material, wherein droplets are generated from liquid including fine particles, a density of particles in said droplets is increased by vaporizing a solvent with an infrared heating source, including using weak laser irradiation, a particle-cluster in which large number of fine particles aggregate is formed after condensation of said droplets, and a pulsed laser for generating a plasma irradiates said particle-cluster.

2. The method according to claim 1, further comprising:

a method of cracking the particle-cluster to disperse aggregating particles prior to plasma generation using at least one of a thermal, an electrical, and a mechanical shock with heating by at least one of the irradiation of a laser and charged particle beam.

3. The method according to claim 1, wherein droplets of liquid including fine particles are formed by giving a vibration to a nozzle through which said liquid is ejected.

4. The method according to claim 1, wherein at least one of a liquid nitrogen, a water, and an organic solvent is employed as a solvent of the suspension liquid.

5. The method according to claim 3, wherein particles in a suspension liquid in a reservoir are uniformly distributed in order to reduce fluctuation of number of particles in the particle-cluster by at least one of controlling the potential of Hydrogen in the suspension liquid and by stirring the suspension.

6. The method according to claim 3, wherein a nozzle ejecting a suspension liquid is vibrated regularly for droplet generation.

7. The method according to claim 6, wherein a frequency of vibration is between 100 Hz and 1 MHz.

8. The method according to claim 6, wherein amplitude of vibration is larger than 1 μm.

9. The method according to claim 3, wherein at least one of vaporization and sublimation of a solvent of a droplet is performed in a separate space before delivering a droplet of a suspension to a plasma generation space.

10. The method according to claim 9, wherein at least one of vaporization and sublimation of a solvent of droplets is enhanced by heating droplets by laser irradiation.

11. The method according to claim 1, further comprising:

a method of charging a particle-cluster; and a method of electrically controlling the trajectory of a particle-cluster.

12. The method according to claim 1, wherein particles constituting a particle-cluster is smaller than 1 μm in diameter.

13. The method according to claim 1, wherein particles constituting a particle-cluster contain at least one of tin, tin oxide, and other tin compounds.

14. The method according to claim 1, wherein a total mass of particles constituting a particle-cluster is larger than that of a single particle with solid-state density having a diameter of 5 μm.

15. The method according to claim 1, wherein a total mass of particles constituting a particle-cluster is smaller than that of a single particle with solid-state density having a diameter of 200 μm.

16. The method according to claim 1, wherein particles constituting a particle-cluster are generated by the laser ablation of at least one of a liquid target and a solid target, including a chemical element comprising said particles.

17. A method for generating a plasma as a source of radiation by irradiating a pulsed laser on material, wherein generation of fine particles by irradiating a short pulse on at least one of a solid target and a liquid target is performed in the environment where a gas flows, and the generated particles are conveyed by the gas flow into a plasma generation space.

18. An apparatus for generating a plasma as a source of radiation by irradiating a pulsed laser on material, wherein droplets are generated from liquid including fine particles, the density of particles in said droplets is increased by vaporizing a solvent with an infrared heating source, including using weak laser irradiation, a particle-cluster in which large number of fine particles aggregate is formed after condensation of said droplets, and a pulsed laser for generating a plasma irradiates said particle-cluster.

19. The apparatus according to claim 18, further comprising:

a method of cracking a particle-cluster to disperse aggregating particles prior to plasma generation using at least one of a thermal, an electrical, and a mechanical shock with heating by at least one of the irradiation of a laser and charged particle beam.

20. The apparatus according to claim 18, wherein droplets of liquid including fine particles is formed by giving a vibration to a nozzle through which said liquid is ejected.

21. The apparatus according to claim 18, wherein at least one of a liquid nitrogen, water, and an organic solvent is employed as a solvent of the suspension liquid.

22. The apparatus according to claim 20, wherein particles in a suspension liquid in a reservoir are uniformly distributed in order to reduce fluctuation of number of particles in a particle-cluster by at least one of controlling the potential of Hydrogen of the suspension and by stirring the suspension.

23. The apparatus according to claim 20, wherein a nozzle ejecting a suspension liquid is vibrated regularly for stable plasma generation.

24. The apparatus according to claim 23, wherein a frequency of vibration is between 100 Hz and 1 MHz.

25. The apparatus according to claim 23, wherein amplitude of vibration is larger than 1 μm.

26. The apparatus according to claim 20, wherein at least one of vaporization and sublimation of a solvent of a droplet is performed in a separate space before delivery to a plasma generation space.

27. The apparatus according to claim 26, wherein at least one of vaporization and sublimation of solvent of droplets is enhanced by heating droplets by laser irradiation.

28. The apparatus according to claim 18, further comprising:

a method of charging a particle-cluster and a method of electrically controlling the trajectory of a particle-cluster.

29. The apparatus according to claim 18, wherein particles constituting a particle-cluster is smaller than 1 μm in diameter.

30. The apparatus according to claim 18, wherein particles constituting a particle-cluster contain at least one of tin, tin oxide, and other tin compounds.

31. The apparatus according to claim 18, wherein a total mass of particles constituting a particle-cluster is larger than that of a single particle with solid-state density having a diameter of 5 μm.

32. The apparatus according to claim 18, wherein a total mass of particles constituting a particle-cluster is smaller than that of a single particle with solid-state density having a diameter of 200 μm.

33. The apparatus according to claim 18, wherein a particles constituting a particle-cluster are generated by the laser ablation of at least one of a liquid target and a solid target.

34. An apparatus for generating a plasma as a source of radiation by irradiating a pulsed laser on material, wherein generation of small particles by irradiating a short pulse on at least one of a solid target and a liquid target is performed in the environment where a gas flows and the generated particles are conveyed by the gas flow into a plasma generation space.

* * * * *